United States Patent [19]

Kakimoto et al.

[11] Patent Number: 4,772,628
[45] Date of Patent: Sep. 20, 1988

[54] ORGANOGERMANIUM COMPOUND AND ANTITUMOR AGENT COMPOSED MAINLY OF THIS COMPOUND

[75] Inventors: Norihiro Kakimoto, Machida; Nobuo Tanaka, Tokyo; Isao Sato; Katsuyuki Sato, both of Komae, all of Japan

[73] Assignee: Asai Germanium Research Institute, Tokyo, Japan

[21] Appl. No.: 946,202

[22] Filed: Dec. 24, 1986

[30] Foreign Application Priority Data

Dec. 28, 1985 [JP] Japan ................ 60-298823
Dec. 28, 1985 [JP] Japan ................ 60-298824

[51] Int. Cl.$^4$ .................. A01N 9/00; C07D 7/30
[52] U.S. Cl. .................. 514/492; 556/83; 556/87; 556/89
[58] Field of Search .................. 556/89, 83, 87; 514/492

[56] References Cited

U.S. PATENT DOCUMENTS

| | | | |
|---|---|---|---|
| 3,786,067 | 1/1974 | Throckmorton et al. | 556/89 X |
| 4,066,678 | 1/1978 | Sato et al. | 556/83 X |
| 4,271,084 | 6/1981 | Ishikawa et al. | 556/83 |
| 4,361,579 | 11/1982 | Munakata et al. | 556/89 X |

FOREIGN PATENT DOCUMENTS

| | | | |
|---|---|---|---|
| 0016444 | 10/1980 | European Pat. Off. | 556/89 UX |
| 0085513 | 8/1983 | European Pat. Off. | 556/89 UX |
| 1365997 | 9/1974 | United Kingdom | 556/89 UX |
| 2158070 | 2/1985 | United Kingdom | 556/89 UX |
| 2143128 | 2/1985 | United Kingdom | 556/89 UX |

OTHER PUBLICATIONS

Chemical Abstracts 92 94518z (1980).
Chemical Abstracts 101 130791y (1984).
Chemical Abstracts 103 178349d (1985).

*Primary Examiner*—Paul F. Shaver
*Attorney, Agent, or Firm*—Burns, Doane, Swecker & Mathis

[57] ABSTRACT

This invention discloses organogermanium compounds characterized in being expressed by the following formula:

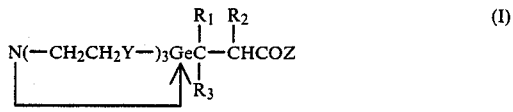

(I)

wherein $R_1$, $R_2$ and $R_3$ respectively denote a hydrogen atom, a lower alkyl group, or a substituted or unsubstituted phenyl group, Y denotes an oxygen or sulfur atom, and Z denotes a hydroxyl group, an amino, or a lower alkoxy group, and antitumor agents comprising as a principal agent these compounds.

16 Claims, No Drawings

ORGANOGERMANIUM COMPOUND AND ANTITUMOR AGENT COMPOSED MAINLY OF THIS COMPOUND

DETAILED DESCRIPTION OF THE INVENTION

The present invention relates to organogermanium compounds and strong antitumor agents composed mainly of these compounds.

PRIOR ART

Although the known metal germanium (Ge) has previously been the object of investigation in the fields of physics and inorganic chemistry, organic compounds thereof have recently been developed and the results of various investigations in this field have been published with increasing frequency. As a result, attention has been directed to germanium, particularly organic compounds thereof, in various technical fields.

For example, it has become known in the field of medicine that carboxyethylgermanium sesquioxide having a sheet form which is expressed by the following formula:

$$(GeCH_2CH_2COOH)_2O_3$$

exhibits excellent physiological activities such as very strong hypotensive and antitumor activities without showing any toxicity and generation of side-effects at all.

On the other hand, the inventors of the present invention have participated in investigations into the development of organogermanium compounds over a long period of time. During these investigations, the inventors discovered carboxyethylgermanium sesquisulfide which is a compound shown by the following formula:

$$(GeCH_2CH_2COOH)_2S_3$$

and found that this compound exhibits antitumor activity. Patent applications in respect of these discoveries have been submitted (refer to Japanese Patent Publication No. 35916/1984 for the former and to Japanese Patent Laid-Open No. 16924/1985 for the latter).

PROBLEMS TO BE SOLVED BY THE INVENTION

However, the mechanism of the above-described carboxyethylgermanium sesquioxide and carboxyethylgermanium sesquisulfide which is responsible for their excellent physiological activities has not been clearly elucidated so far, but since the bond between germanium and the oxygen or sulfur atom is presented by both of these two compounds, and it is considered to play a large role in these physiological activities. Thus, it can be reasonably expected that similar or completely different physiological activities will be found with respect to similar compounds having a bond between germanium and an oxygen or sulfur atom.

MEANS FOR SOLVING THE PROBLEMS

The present invention has been achieved against the background of the above-described prior art and with a view to providing compounds having the above-described bond between germanium and an oxygen or sulfur atom, as well as being directed to their application as antitumor agents. The structures of these compounds are characterized in that they are expressed by the following formula:

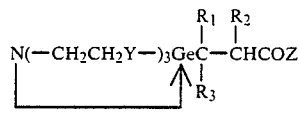

wherein $R_1$, $R_2$ and $R_3$ respectively denote a hydrogen atom, a lower alkyl group such as methyl or ethyl group, or a substituted or unsubstituted phenyl group, Y denotes an oxygen atom or a sulfur atom, and Z denotes a hydroxyl group, an amino group, or a lower alkoxy group. Applications of these compounds are characterized by comprising as principal agents organogermanium compounds expressed by the following formula:

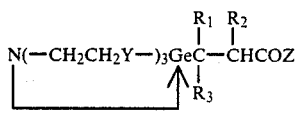

wherein $R_1$, $R_2$ and $R_3$ respectively denote a hydrogen atom, a lower alkyl group such as a methyl or ethyl group, or a substituted or unsubstituted phenyl group, Y denotes an oxygen atom or a sulfur atom, and Z denotes a hydroxyl group, an amino group, or a lower alkoxy group.

The present invention is described in detail hereinafter.

Firstly, description is made of the organogermanium compounds of the present invention, in which derivatives of propionic acid having substituents $R_1$, $R_2$, and $R_3$ and an oxygen functional group Z,

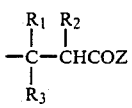

are bonded with atlane skeleton,

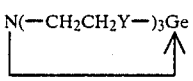

i.e. germatlane skeleton, comprising a crosslinking between the germanium and the nitrogen atoms through three dimethylene groups and a coordination of the electron pair of the nitrogen atom with the germanium atom.

Among the above-described substituted groups, $R_1$, $R_2$ and $R_3$ independently denote a hydrogen atom, a lower alkyl group such as a methyl, ethyl, or propyl group, or a substituted or unsubstituted phenyl group, Z denotes a hydroxyl group, an amino group, or a lower alkoxy group, and Y denotes an oxygen atom or sulfur atom.

The organogermanium compounds having the above-described structure can be produced by various methods.

For example, the substituents $R_1$, $R_2$, $R_3$, and Z may be previously introduced into the carboxyethylgermanium sesquioxide (1) or the carboxyethylgermanium sesquisulfide (2) and the resulting product may then be reacted with any nitrogen compound (3), as shown in the following reaction formula 1:

Reaction formula 1
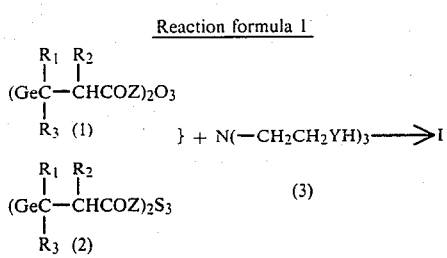

In addition, the corresponding trichloro compound (4) may be changed to the trialkoxy compund (5) and then reacted with the above-described nitrogen compound (3), as shown in the following reaction formula 2:

Reaction formula 2
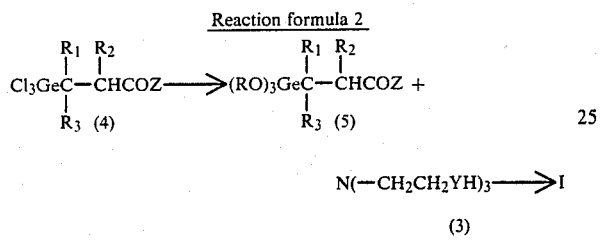

The organogermanium compounds obtained in such a manner are generally crystalline compounds and the results of instrumental analyses such as nuclear magnetic resonance absorption spectra and infrared absorption spectra sufficiently support the fact that the above-described compounds are those shown by the formula I.

Typical examples of the organogermanium compounds obtained in accordance with the above-described methods involve in the following compounds.

Firstly, compounds obtained in the case of Y=O and Z=NH$_2$ include compounds in which nitrogen and germanium atoms are bonded through three oxymethylene groups, as shown below.

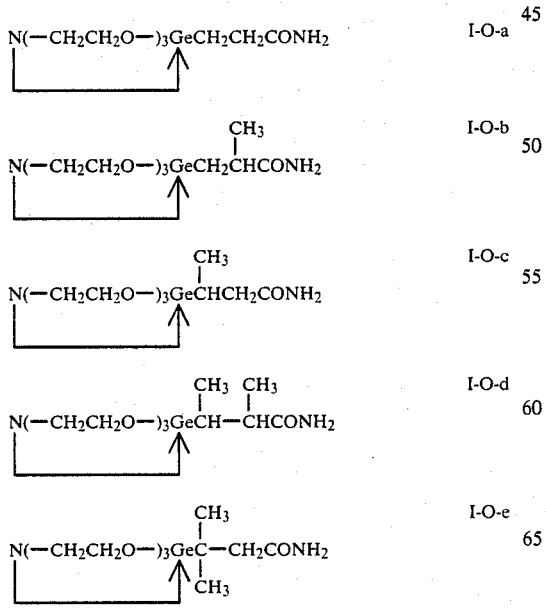

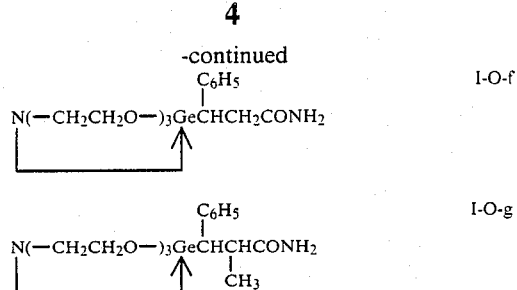

In the case of Y=S, the following compounds are obtained, wherein the nitrogen and germanium atoms are bonded through three thiomethylene groups.

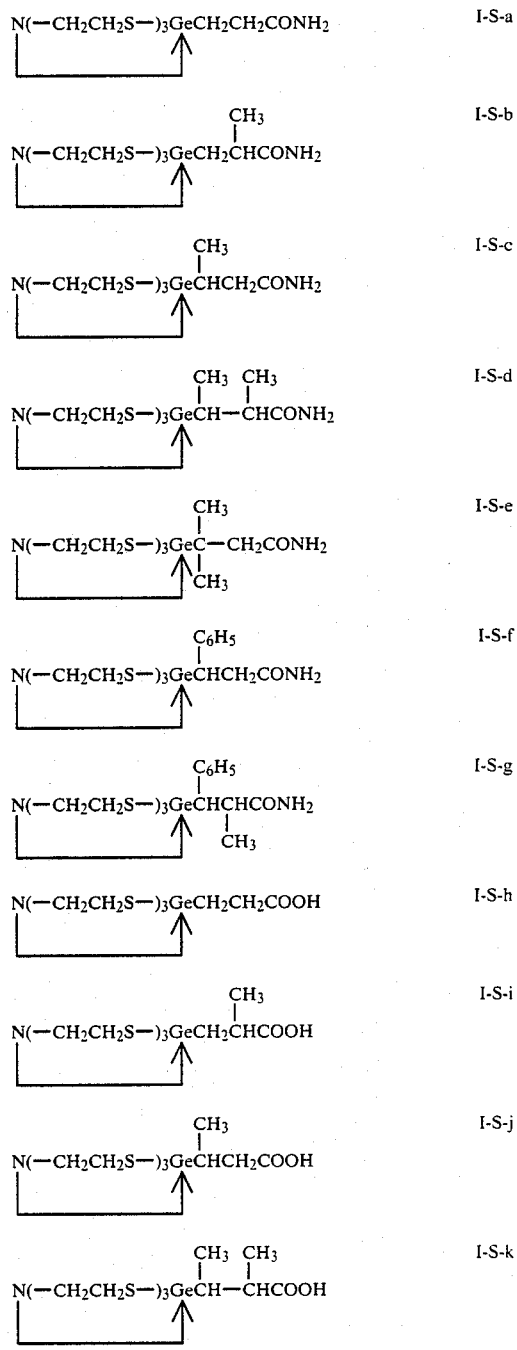

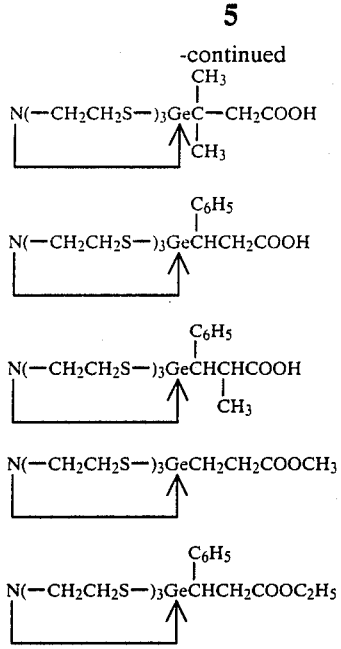

EFFECTS AND FUNCTIONS OF THE INVENTION

Current therapies for tumors mainly involve surgical therapy, radiotherapy, and administration of antitumor agents. With respect to antitumor agents, many conventional chemistry agents damage tumor cells as well as normal cells, and thus the development of medicines exhibiting antitumor activities on the basis of a mechanism which is completely different from these chemistry agents has been vigorously pursued in recent days. Interferons which are a form of immunotherapy agents are examples of such medicines.

In a similar manner, the above-described carboxyethylgermanium sesquioxide may also be used clinically as an antitumor agent of a completely new type and it is considered that the antitumor activities exhibited by the above-described carboxyethylgermanium sesquisulfide are caused by a similar mechanism to that of the sesquioxide. Such compounds are, however, classified into a BRM (Biological Response Modifiers), and it is known that these compounds react sensitively with IMC-Carcinoma, which is the ascitic tumor cell of a $CDF_1$ mouse.

The inventors of the present invention conducted screening of compounds which could be used as the BRM other than the above-described carboxyethylgermanium sesquioxide and the above-described carboxyethyl-germanium sesquisulfide in a system using the IMC-Carcinoma against the background of the above-described situation. The inventors consequently found that the above-described organogermanium compounds having the atlane skeleton exhibited a strong inhibition effect on the IMC-Carcinoma, leading to the achievement of the present invention.

EXAMPLES

The present invention is described in detail with reference to the following examples.

EXAMPLE 1. SYNTHESIS OF ORGANOGERMANIUM COMPOUND I-O-a 7.28 g (0.029 mol) of trichlorogermylpropionic amide was dissolved in 50 ml of an anhydrous ethanol and a sodium methoxide solution which had been previously prepared by dissolving 2.0 g (0.087 mol) of metal sodium in 100 ml of an anhydrous ethanol was gradually added to the resulting solution at room temperature under agitation.

The reaction solution generated a slight amount of heat and a salt was precipitated therefrom.

After completion of the reaction, the methanol was removed by distillation at a reduced pressure until the volume of the solution reached about 50 ml. Then, the precipitated salt was filtered and washed with about 20 ml of an anhydrous methanol. The solution used for washing the salt was mixed with the filtrate and an anhydrous methanol was added to the solution obtained util the total volume became about 300 ml.

4.3 g (0.029 mol) of triethanol amine was added to the resulting anhydrous methanol solution and subjected to reflux heating for about 6 hours. After the solution had cooled, methanol was removed by distillation to obtain crude white crystals. The crystals obtained were recrystallized from 100 ml of chloroform to obtain 5.2 g of the compound (I-O-a), with a yield of 62%.

| Compound I-O-a | |
|---|---|
| Melting point: | 177° C. |
| IR (KBr, cm$^{-1}$): | 3500–3200, 1660, 1620, 930, 900, 870 |
| NMR (CD$_3$OD, ppm) | 1.08 (2H, t) |
| | 2.48 (2H, t) |
| | 2.91 (6H, t) |
| | 3.75 (6H, t) |

The other compounds (I-O-b) and (I-O-g) were successfully synthesized either by the above-described method or the method shown by the reaction formula 1 and exhibited the physical properties shown in Table 1.

EXAMPLE 2. SYNTHESIS OF ORGANOGERMANIUM COMPOUND I-S-d 2.8 g (0.01 mol) of (1,2-dimethyl)-trichlorogermyl-propionic amide was dissolved in anhydrous ethanol and 2.04 g (0.03 mol) of sodium ethoxide which had been previously prepared by dissolving it in anhydrous ethanol was gradually added to the solution obtained and agitated for 1 hour under the anhydrous condition.

Then, 1.97 g (0.001 mol) of trithioethanol amine was added to the resulting solution and refluxed for 8 hours.

After completion of the reaction, the crystals produced were filtered off, dissolved in a mixed solution of 200 ml of chloroform and 100 ml of water, and agitated for a while. Then, the chloroform layer was isolated, washed with a saturated salt water, and dried with anhydrous sodium sulfate. The solvent was removed by distillation to obtain 2.3 g of the organogermanium compound (I-S-d) used in the present invention, with a yield of 62.7%.

| Compound I-S-d | |
|---|---|
| Melting point: | 179–181° C. |
| IR (KBr, cm$^{-1}$): | 3400–3200, 1680, 1660, 1630, 390 |
| NMR (DMSO-d$_6$, ppm): | 1.06 (3H, d) |
| | 1.20 (3H, d) |
| | 1.46 (1H, m) |
| | 2.30 (1H, m) |
| | 2.63 (12H, m) |

The other compounds I-S-a to I-S-c and I-S-e to I-S-g were successfully synthesized by the above-described method or the method shown by the reaction formula 1, and exhibited the physical properties shown in Table 2.

EXAMPLE 3. SYNTHESIS OF ORGANOGERMANIUM COMPOUND I-S-h 5.8 g (0.03 mol) of trithioethanol amine was added to 5.0 g (0.0147 mol) of carboxyethylgermanium sesquisulfide and subjected to reflux heating in benzene for 5 hours.

After completion of the reaction, the precipitated crystals were filtered off and recrystallized from a mixed solution of methanol-ether to obtain crystals of the organogermanium compound I-S-h used in the present invention, with a yield of 51%.

| Compound I-S-h | |
| --- | --- |
| Melting point: | 167° C. |
| IR (KBr, cm$^{-1}$) | 3400, 1700, 400, 370 |
| NMR (CDCl$_3$, ppm) | 1.46 (2H, t) |
| | 2.58 (2H, t) |
| | 2.70 (12H, m) |

The other compounds I-S-i to I-S-n were successfully synthesized by using either the above-described method or the method shown by the reaction formula 1 and exhibited the physical properties shown in Table 3.

EXAMPLE 4. SYNTHESIS OF ORGANOGERMANIUM COMPOUND I-S-o 2.0 g (7.6 mmol) of methyl trichlorogermylpropionate was dissolved in 10 ml of methanol and 50 ml of a sodium methoxide solution prepared from metal sodium, as required, was added to the resulting mixture to precipitate sodium chloride while generating a slight amount of heat.

After completion of the reaction, sodium chloride was filtered off and a solution obtained by dissolving 1.5 g (7.6 mmol) of trithioethanol amine in 30 ml of chloroform was gradually added to the filtrate obtained at −30° C., agitated at room temperature for about 1 hour, and then subjected to reflux heating for 2 hours.

After completion of the reaction, the solvent was removed by distillation leaving an oily substance. This substance was later crystallized and recrystallized to obtain the compound (I-S-o), with a yield of 61%.

The other cmpounds were successfully synthesized by synthetic operations which were substantially the same as those of the above-described method.

| Compound I-S-o | |
| --- | --- |
| Melting point: | 87° C. |
| IR (KBr, cm$^{-1}$) | 1710, 390, 360 |
| NMR (CDCl$_3$, ppm) | 1.46 (2H, t) |
| | 2.53 (2H, t) |
| | 2.70 (12H, s) |
| | 3.63 (3H, s) |

| Compound I-S-p | |
| --- | --- |
| Melting point: | 105–107° C. |
| IR (KBr, cm$^{-1}$) | 1730, 400, 380 |
| NMR (CDCl$_3$, ppm) | 1.03 (3H, t) |
| | 2.30–2.90 (12H, m) |
| | 3.03 (3H, s) |
| | 3.94 (2H, q) |
| | 7.20 (5H, m) |

EXAMPLE 5, PHARMACEUTICAL EFFECT OF AGENTS OF THE PRESENT INVENTION

IMC-Carcinoma was subcutaneously implanted in the inguinal region of a group of 10 CDF$_1$-type mice (9 weeks old, ♀) at a rate of $1 \times 10^6$ cells/mouse and the above-described organogermanium compounds in a 0.5% CMC suspension were then perorally administered to the mice daily at a rate of 1 to 100 mg per day during the periods of first to 5th days, 7th to 12th days, 14th to 19th days. When the respective weights of tumor were measured after 21 days has passed and the inhibition rates relative to a central group were calculated, it was found that the optimum amount of the organogermanium compounds to be administered during the inhibition of the proliferation of IMC-Carcinoma was very small.

Examples are shown in Tables 4a, 4b. The excellent features of the agents of the present invention are clear when it is considered that the optimum amount of conventional pharmaceuticals of this type to be administered is about 100 mg.

TABLE 1

| Compound | Melting Point | IR(KBr, cm$^{-1}$) | NMR(ppm) [Solvent] | Yield |
| --- | --- | --- | --- | --- |
| I—O-b | 201° C. | 3400, 3200, 1670, 930, 900 580 | 1.00(1H, dd), 1.20(3H, d) 1.26(1H, dd), 2.76(1H, m) 2.90(6H, t), 3.73(6H, t) [DMSO-d$_6$] | 60% |
| I—O-c | 221° C. | 3300, 3150, 1670, 935, 910, 570, 560, | 1.20(3H, d), 1.60(1H, m) 2.20, 2.70(2H, m) 2.93(6H, t), 3.76(6H, t) [CD$_3$OD] | 85% |
| I—O-D | 196° C. | 3400–3200 1690, 1660 920, 910 585, 575 | 1.00(3H, d), 1.10(3H, d) 1.30(1H, m), 2.30(1H, m) 2.76(6H, t), 3.60(6H, t) [DMSO-d$_6$] | 55% |
| I—O-e | 205° C. | 3400–3200 1670, 1635 940, 900 575 | 1.13(6H, s), 2.26(2H, s) 2.85(6H, t), 3.53(6H, t) [DMSO-d$_6$] | 70% |
| I—O-f | 228° C. | 3400–3200 1680, 1660 945, 905 580 | 2.90(3H, s), 2.85(6H, t) 3.70(6H, t), 7.15(5H, m) [CD$_3$OD] | 86% |
| I—O-g | 211–213° C. | 3450–3170 1670, 1620 940, 905 585, 570 | 1.20(3H, d), 2.60–3.10(2H, m) 2.73(6H, t), 3.53(6H, t) 6.80–7.26(5H, m) | 65% |

TABLE 1-continued

| Compound | Melting Point | IR(KBr, cm$^{-1}$) | NMR(ppm) [Solvent] | Yield |
|---|---|---|---|---|
| | | | [DMSO-d$_6$] | |

The values of elemental analyses agree with the calculated values within the rage of carbon; ±0.5, hydrogen; ±0.3 and germanium; ±0.3.

TABLE 2

| Compound | Melting Point | IR(KBr, cm$^{-1}$) | NMR(ppm) [Solvent] | Yield |
|---|---|---|---|---|
| I—S-a | 194° C. | 3400–3150<br>1660, 1620<br>395, 360 | 1.10–1.30(2H, m)<br>2.15–2.35(2H, m)<br>2.70(12H, brs)<br>[DMSO-d$_6$] | 55% |
| I—S-b | 200° C. | 3400–3170<br>1660<br>420, 400 | 1.10(3H, d), 1.10(1H, dd)<br>1.30(1H,dd), 2.56(1H, m)<br>2.66(12H, m)<br>6.53, 7.10(2H,br)<br>[DMSO-d$_6$] | 60% |
| I—S-c | 189–192° C. | 3400–3150<br>1670, 1620<br>400 | 1.03(3H, d),<br>1.40–1.73(1H, m)<br>1.86(1H, dd), 2.03(1H,dd)<br>2.66(12H, m)<br>[DMSO-d$_6$] | 77% |
| I—S-e | 224° C. | 3450–3200<br>1680, 1660<br>1620, 405 | 1.26(6H, s), 2.33(2H, s)<br>2.70(12H, m)<br>[ACETON-d$_6$] | 70% |
| I—S-f | 249–252° C. | 3400–3200<br>1670<br>395 | 2.60(12H, m)<br>2.60–2.90(3H, m)<br>7.13(5H, m)<br>[DMSO-d$_6$] | 70% |
| I—S-g | 235° C. | 3400–3200<br>1675<br>400 | 1.36(3H, d)<br>2.10–2.80(13H, m)<br>3.00(1H, m)<br>7.10(5H, m)<br>[DMSO-d$_6$] | 53% |

The values of elemental analyses agree with the calculated values within the rage of carbon; ±0.5, hydrogen; ±0.3 and germanium; ±0.3.

TABLE 3

| Compound | Melting Point | IR(KBr, cm$^{-1}$) | NMR(ppm) [Solvent] | Yield |
|---|---|---|---|---|
| I—S-i | 135° C. | 3400<br>1700<br>400, 380 | 1.28(3H, d), 1.35(1H, dd)<br>1.76(1H, dd)<br>2.60–2.90(1H, m)<br>2.70(12H, s)<br>[CDCl$_3$] | 60% |
| I—S-j | 175° C. | 3400<br>1700<br>400, 380 | 1.17(3H, d)<br>1.40–1.90(1H, m)<br>2.16(1H, dd) 2.75(1H, dd)<br>2.73(12H, s)<br>[ACETON-d$_6$] | 77% |
| I—S-k | 133° C. | 3400<br>1700<br>390 | 1.25(3H, d), 1.33(3H, d)<br>1.80(1H, brq)<br>2.76(1H, brq)<br>2.68(12H, s)<br>[CDCl$_3$] | 62% |
| I—S-l | 148° C. | 3400<br>1705<br>405, 395 | 1.26(6H, s), 2.48(2H, s)<br>2.72(12H, s),<br>[ACETON-d$_6$] | 55% |
| I—S-m | 194° C. | 3400<br>1695<br>400, 380 | 2.20–2.80(2H, m)<br>2.63(12H, s)<br>7.16(5H, brs)<br>[DMSO-d$_6$] | 84% |
| I—S-n | 121° C. | 3400<br>1700<br>400, 390 | 1.50(3H, d), 2.36(1H, dq)<br>2.60–2.90(12H, m)<br>7.23(5H, m)<br>[CDCl$_3$] | 72% |

The values of elemental analyses agree with the calculated values wihtin the rage of carbon; ±0.5, hydrogen; ±0.3 and germanium; ±0.3.

TABLE 4a

| Compound | Administration amount (mg/Kg) | Tumor weight (average ± S.D) | Inhibition rate (%) |
|---|---|---|---|
| Control group | — | 1.46 ± 0.53 | — |
| I-O-a | 50 | 1.62 ± 0.64 | — |
| | 10 | 1.14 ± 0.69 | 22 |
| | 2 | 1.11 ± 0.48 | 24 |
| I-O-c | 5 | 0.87 ± 0.42 | 40** |
| I-O-f | 1 | 0.79 ± 0.46 | 46** |
| | 100 | 1.19 ± 1.03 | 18 |

TABLE 4a-continued

| Compound | Administration amount (mg/Kg) | Tumor weight (average ± S.D) | Inhibition rate (%) |
|---|---|---|---|
| | 10 | 1.20 ± 0.28 | 18 |

\*\*$P < 0.01$

TABLE 4b

| Compound | Administration amount (mg/Kg) | Tumor weight (average ± S.D) | Inhibition rate (%) |
|---|---|---|---|
| Control group | — | 1.46 ± 0.53 | — |
| I-S-a | 5 | 1.33 ± 0.48 | 9 |
| | 1 | 1.54 ± 0.70 | — |
| I-S-c | 5 | 1.28 ± 0.49 | 12 |
| | 1 | 1.09 ± 0.42 | 25 |
| I-S-f | 5 | 1.00 ± 0.48 | 32\* |
| | 1 | 1.07 ± 0.46 | 27 |
| I-S-g | 5 | 1.40 ± 0.65 | 4 |
| | 1 | 1.16 ± 0.31 | 21 |
| I-S-m | 5 | 1.09 ± 0.51 | 25 |
| | 1 | 1.04 ± 0.32 | 29\* |

\*$P < 0.05$

I claim:

1. Organogermanium compound having the following formula:

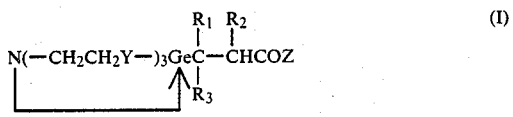

(I)

wherein $R_1$, $R_2$ and $R_3$ respectively denote a hydrogen atom, a lower alkyl group, or a substituted or unsubstituted phenyl group, Y denotes an oxygen or sulfur atom, and Z denotes a hydroxyl group, an amino, or a lower alkoxy group wherein if Y is an oxygen atom and Z is a hydroxy group, an amino group or a lower alkoxy group, $R_1$, $R_2$ and $R_3$ cannot all be hydrogen.

2. The organogermanium compound according to claim 1, in which Y=O.

3. The organogermanium compound according to claim 2, in which $R_1$ is selected from a hydrogen atom, a lower alkyl group, and a phenyl group, and $R_2$ and $R_3$ are independently selected from a hydrogen atom and a lower alkyl group.

4. The organogermanium compound according to claim 3, in which $Z=NH_2$.

5. The organogermanium compound according to claim 1, in which Y=S.

6. The organogermanium compound according to claim 5, in which $R_1$ is selected from a hydrogen atom, a lower alkyl group, and a phenyl group, and $R_2$ and $R_3$ are independently selected from a hydrogen atom and a lower alkyl group.

7. The organogermanium compound according to claim 6, in which $Z=NH_2$.

8. The organogermanium compound according to claim 6, in which Z=—OH.

9. The organogermanium compound according to claim 6, in which Z=—O—lower alkyl group.

10. A pharmaecutical composition of matter for use as an antitumor agent, said composition comprising an antitumor effective amount of an organogermanium compound having the following formula:

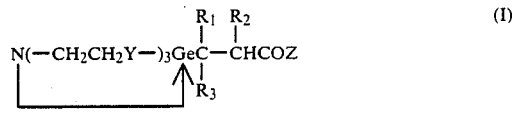

(I)

wherein $R_1$, $R_2$ and $R_3$ respectively denote a hydrogen atom, a lower alkyl group, or a substituted or unsubstituted phenyl group, Y denotes an oxygen atom or a sulfur atom, and Z denotes a hydroxyl group, an amino group, or a lower alkoxy group with the proviso that $R_1$, $R_2$ and $R_3$ cannot all be a hydrogen atom if Y denotes an oxygen atom and Z is an ethoxy group, and a pharmaceutically acceptable carrier.

11. The pharmaceutical composition according to claim 10 wherein Y=O.

12. The pharmaceutical composition according to claim 10 wherein Y=S.

13. A method for treating a tumor in a mammal, said method comprising administering to said mammal an antitumor effective amount of an organogermanium compound having the following formula:

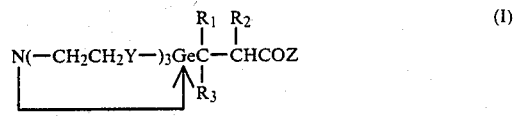

(I)

wherein $R_1$, $R_2$ and $R_3$ respectively denote a hydrogen atom, a lower alkyl group, or a substituted or unsubstituted phenyl group, Y denotes an oxygen atom or a sulfur atom, and Z denotes a hydroxyl group, an amino group, or a lower alkoxy group with the proviso that $R_1$, $R_2$ and $R_3$ cannot all be a hydrogen atom if Y denotes an oxygen atom and Z is an ethoxy group, and a pharmaceutically acceptable carrier.

14. The method according to claim 13 wherein said tumor is IMC-Carcinoma.

15. The method according to claim 13 wherein Y=O.

16. The method according to claim 13 wherein Y=S.

\* \* \* \* \*